(12) United States Patent
Hubelbank et al.

(10) Patent No.: US 11,696,795 B2
(45) Date of Patent: Jul. 11, 2023

(54) AMPLITUDE MODULATED WAVEFORM CIRCUITRY FOR ELECTROSURGICAL DEVICES AND SYSTEMS, AND RELATED METHODS

(71) Applicant: Medtronic Advanced Energy LLC, Minneapolis, MN (US)

(72) Inventors: David Hubelbank, Portsmouth, NH (US); Jeffrey Reaume, Portsmouth, NH (US); Alexander Segit, Eliot, ME (US); Tyler Clark, Brentwood, NH (US)

(73) Assignee: MEDTRONIC ADVANCED ENERGY LLC, Minneapolis, MN (US)

( * ) Notice: Subject to any disclaimer, the term of this patent is extended or adjusted under 35 U.S.C. 154(b) by 487 days.

(21) Appl. No.: 16/507,563

(22) Filed: Jul. 10, 2019

(65) Prior Publication Data

US 2020/0015877 A1 Jan. 16, 2020

Related U.S. Application Data

(60) Provisional application No. 62/697,649, filed on Jul. 13, 2018.

(51) Int. Cl.
| | |
|---|---|
| A61B 18/12 | (2006.01) |
| H03K 3/02 | (2006.01) |
| H03H 7/01 | (2006.01) |
| H03K 17/687 | (2006.01) |
| A61B 18/14 | (2006.01) |
| A61B 17/00 | (2006.01) |

(Continued)

(52) U.S. Cl.
CPC ...... *A61B 18/1206* (2013.01); *A61B 18/1402* (2013.01); *H03H 7/0115* (2013.01); *H03K 3/02* (2013.01); *H03K 17/687* (2013.01); *A61B 2017/00141* (2013.01); *A61B 2017/00172* (2013.01); *A61B 2018/00589* (2013.01); *A61B 2018/00601* (2013.01); *A61B 2018/00607* (2013.01); *A61B 2018/00767* (2013.01); *A61B 2018/1273* (2013.01); *H02M 7/42* (2013.01); *H03H 7/175* (2013.01); *H03H 7/1775* (2013.01)

(58) Field of Classification Search
CPC ............ A61B 18/1206; A61B 18/1402; A61B 2017/00141; A61B 2017/00172; A61B 2018/00607; A61B 2018/00767; A61B 2018/1273; H03H 7/0115; H03K 3/02; H02M 7/42
See application file for complete search history.

(56) References Cited

U.S. PATENT DOCUMENTS

| | | | | |
|---|---|---|---|---|
| 4,438,766 | A * | 3/1984 | Bowers | A61B 18/1206 606/37 |
| 4,727,874 | A * | 3/1988 | Bowers | A61B 18/1206 330/251 |

(Continued)

FOREIGN PATENT DOCUMENTS

EP 0517243 A1 * 12/1992 ............. F21V 11/00

*Primary Examiner* — Daniel W Fowler
(74) *Attorney, Agent, or Firm* — Patterson Thuente, P.A.

(57) ABSTRACT

Embodiments relate to circuitry to provide amplitude modulated waveforms in electrosurgical devices. The circuitry can be included in an electrosurgical generator device to provide the amplitude modulated waveforms to an electrosurgical probe coupled with the electrosurgical generator device.

3 Claims, 5 Drawing Sheets

(51) Int. Cl.
*A61B 18/00* (2006.01)
*H02M 7/42* (2006.01)

(56) References Cited

U.S. PATENT DOCUMENTS

| | | | |
|---|---|---|---|
| 6,277,083 B1 * | 8/2001 | Eggers | A61B 18/1482 |
| | | | 600/564 |
| 6,620,157 B1 * | 9/2003 | Dabney | A61B 18/16 |
| | | | 606/49 |
| 9,018,983 B2 | 4/2015 | Vankov | |
| 2004/0030328 A1 * | 2/2004 | Eggers | A61B 18/1206 |
| | | | 606/49 |
| 2004/0260279 A1 * | 12/2004 | Goble | A61B 18/1442 |
| | | | 606/41 |
| 2007/0066971 A1 * | 3/2007 | Podhajsky | A61B 18/1402 |
| | | | 606/34 |
| 2009/0306642 A1 | 12/2009 | Vankov | |
| 2010/0196343 A1 * | 8/2010 | O'Neil | A61K 8/66 |
| | | | 424/94.4 |
| 2012/0271304 A1 * | 10/2012 | Werner | A61B 18/1233 |
| | | | 606/45 |
| 2013/0237982 A1 * | 9/2013 | Rencher | A61B 18/10 |
| | | | 606/45 |
| 2014/0002142 A1 | 1/2014 | Vankov | |
| 2014/0074090 A1 * | 3/2014 | Lam | A61B 18/042 |
| | | | 606/49 |
| 2017/0000553 A1 * | 1/2017 | Wiener | A61B 18/1445 |
| 2017/0119452 A1 * | 5/2017 | Ellman | A61B 18/1206 |
| 2017/0126011 A1 * | 5/2017 | Jussila | H02M 7/42 |

\* cited by examiner

AMPLITUDE MODULATED WAVEFORM CIRCUITRY FOR ELECTROSURGICAL DEVICES AND SYSTEMS, AND RELATED METHODS

RELATED APPLICATION

This application claims the benefit of U.S. Provisional Application No. 62/697,649 filed on Jul. 13, 2018, the entirety of which is incorporated herein by reference.

TECHNICAL FIELD

This disclosure relates generally to electrosurgical devices and more particularly to circuitry to provide amplitude modulated waveforms in electrosurgical devices.

BACKGROUND

Electrosurgical devices generally include a handpiece (handle) ergonomically adapted for ease of manipulation by a surgeon during surgery, and for positioning an energy tip of the device to deliver electrical energy to a target tissue for tissue cutting or coagulation. An electrode and electrical supply cable are generally disposed within the handpiece, traversing from the handpiece's proximal end through the handpiece body, and terminating in an energy discharge probe at the distal end of the device. The electrical supply cable typically is connected to an energy source, such as a radiofrequency (RF) energy generator, which supplies a train of high frequency pulses to the probe of the device.

A challenge in electrosurgery is preventing excessive application of heat to the tissue being cut, fulgurated, desiccated, etc., since this tends to produce undesirable affects such as charring and collateral tissue damage. This is typically caused by high temperatures induced by the application of the electrical energy.

Some highly localized high temperature is required during, for instance, tissue coagulation (i.e., sealing) for denaturation of blood and vascular tissue (veins and arteries) followed by occlusions of the blood vessels. Typically desiccation occurs below or close to 100° C. and fulguration at higher temperatures above 100° C. A high temperature during fulguration outside the immediate area being treated can result in undesirable tissue charring and build-up of debris on the electrosurgical probe, which decreases its efficiency of coagulation. This may also result in adhesion of charred tissue to the probe and damage to the areas of the probe with low melting temperatures such as plastic components. Typically this might require cleaning of the probe after each session of coagulation. Also, high temperature may result in smoke obscuring the surgical field, especially for laparoscopic procedures.

SUMMARY

Embodiments relate to circuitry to provide amplitude modulated waveforms in electrosurgical devices, and related systems and methods.

In one embodiment, an electrosurgical generator comprises first generator circuitry configured to produce a first power signal having a first peak voltage; second generator circuitry configured to produce a series of burst signals that, when each burst signal is combined with the first power signal, has a second peak voltage greater than the first peak voltage; and third generator circuitry configured to communicate a signal comprising a combination of the series of burst signals with the first power signal to an electrosurgical probe.

In another embodiment, an electrosurgical system comprises an electrosurgical signal generator operable to generate an amplitude modulated power signal comprising a first sinusoidal signal portion having a first peak voltage and a plurality of second sinusoidal signal portions, the amplitude modulated power signal having a second peak voltage greater than the first peak voltage during the plurality of second sinusoidal signal portions; and an electrosurgical probe electrically coupled with the electrosurgical signal generator to receive the amplitude modulated power signal and apply the amplitude modulated power signal as an output.

In yet another embodiment, a method comprises assembling an electrosurgical signal generator operable to generate an amplitude modulated power signal comprising a first sinusoidal signal portion having a first peak voltage and a plurality of second sinusoidal signal portions, the amplitude modulated power signal having a second peak voltage greater than the first peak voltage during the plurality of second sinusoidal signal portions; and providing an output on the electrosurgical signal generator to electrically couple the electrosurgical signal generator with an electrosurgical probe to provide the amplitude modulated power signal to the electrosurgical probe.

The above summary is not intended to describe each illustrated embodiment or every implementation of the subject matter hereof. The figures and the detailed description that follow more particularly exemplify various embodiments.

BRIEF DESCRIPTION OF THE DRAWINGS

Subject matter hereof may be more completely understood in consideration of the following detailed description of various embodiments in connection with the accompanying figures, in which.

While various embodiments are amenable to various modifications and alternative forms, specifics thereof have been shown by way of example in the drawings and will be described in detail. It should be understood, however, that the intention is not to limit the claimed inventions to the particular embodiments described. On the contrary, the intention is to cover all modifications, equivalents, and alternatives falling within the spirit and scope of the subject matter as defined by the claims.

DETAILED DESCRIPTION OF THE DRAWINGS

The entire contents of U.S. application Ser. No. 12/136,683 and U.S. Pat. No. 9,018,983 are incorporated herein by reference.

Unless the context indicates otherwise, the following terms shall have the following meaning and shall be applicable both to the singular and plural:

The terms "radiofrequency energy" or "RF energy" mean energy from the electromagnetic spectrum having a frequency between about 3 kilohertz (3 kHz) and about 300 gigahertz (300 GHz).

The term "electrosurgical device" means an electrical device designed for handheld use by a surgeon to dispense RF or other energy through the tip of an electrode into target surgical tissue, in order to cut or coagulate the tissue during a surgical procedure.

The term "proximal" or "proximate," in the context of an area or end of a device or element means the operator end of the device or element, while the term "distal" means the patient end of the device or element.

In high voltage electrosurgery, high voltage RF electrical energy is applied to an electrosurgical probe for tissue coagulation and cutting. Energy is intended primarily for use with electrosurgical coagulation but can be used for simultaneous tissue cutting and coagulation.

The electrosurgery probe itself can be of the types disclosed herein, in the above-referenced patents or patent applications, or other types as known in the field. Typically the probe has a relatively small surface area at its active electrode portion (tip) to minimize heating of the tissue being treated. The probe can be mono-polar or bi-polar, and it can be uninsulated (i.e., bare metal), metal or another material at least partially coated with a high dielectric insulating layer, such as glass. In some applications the probe is immersed in the tissue being operated on, which has naturally occurring interstitial fluid present, or some type of liquid is provided immediately around the probe in the surgical field. In other uses for, e.g., fulguration, no liquid is present.

During electrosurgery, rapid heating of the tissue can cause explosive vaporization of interstitial fluid, with the vapor sheath being ionized and forming conductive plasma if the voltage applied is sufficiently high (e.g., greater than about 400 V peak-to-peak in some embodiments). Current flowing from the probe tip through the plasma and into the tissue, and fast heating of the tissue, results in the tissue being vaporized and fragmented. The fragments are ejected, providing tissue cutting. Too much voltage or current applied to the tissue, however, can cause damage, such as thermal injury to collateral tissue.

For tissue coagulation purposes, however, some amount of charring is in fact desirable since that is the intent of coagulation (i.e., to seal tissue). However, tissue charring is undesirable beyond the immediate area being coagulated. Thus, a goal is to maintain a relatively low probe temperature and hence minimize heat transfer to the surrounding tissue while still accomplishing coagulation, desiccation or fulguration.

Additional advantages can be sought in the RF power that is provided to the probe. In particular, it can be advantageous for electrosurgical devices to provide "clean" cutting that minimizes collateral tissue damage. In some embodiments discussed herein, electrosurgical devices require less power and therefore can have fewer thermal effects on tissue at the same cutting drag (e.g., the force or effort required to be exerted on the probe to cut or otherwise affect the tissue as desired).

Figure 1:
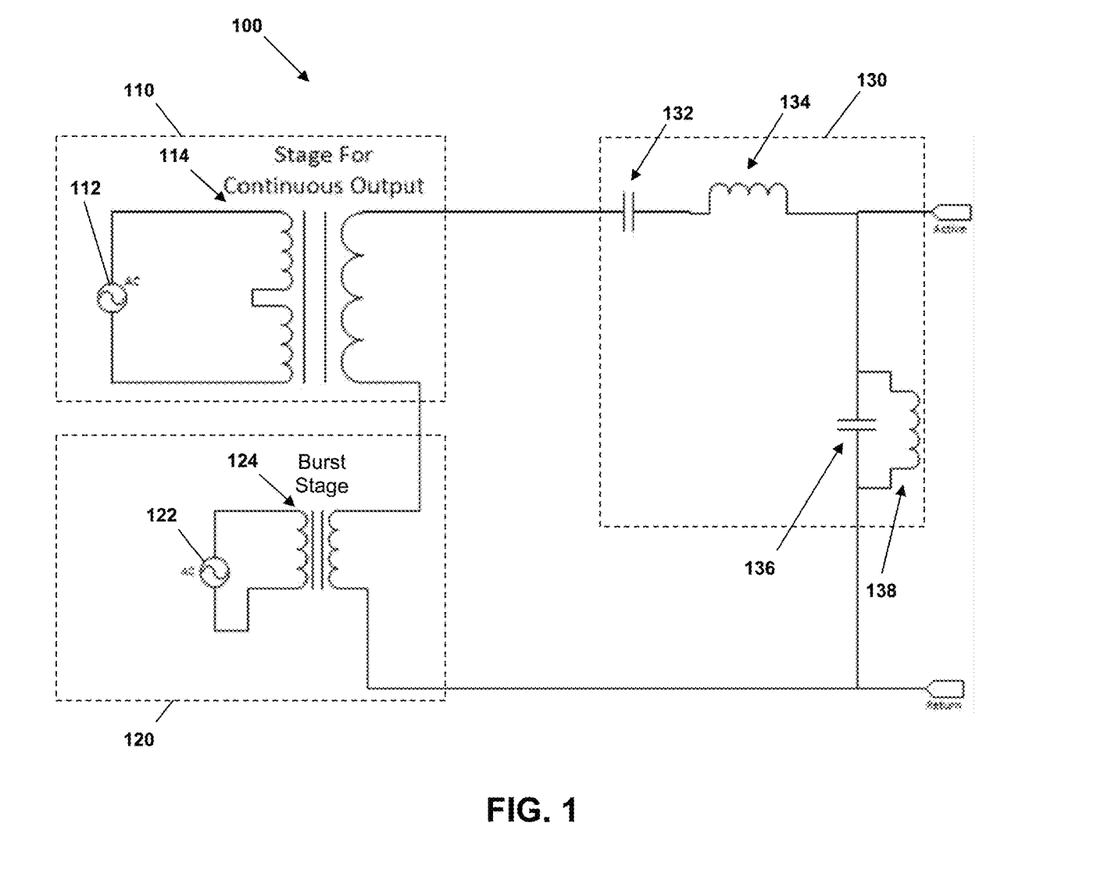
FIG. 1 depicts a transformer circuit diagram according to an embodiment.

Referring to FIG. 1, one embodiment of electrosurgery generator circuitry 100 is depicted. Circuitry 100 comprises a first transformer stage 110, a second transformer stage 120 and output filter circuitry 130.

First transformer stage 110 comprises an alternative current (AC) generator 112 and a transformer 114. Generator 112 provides a power signal to a first, low voltage side of transformer 114. The signal generated by generator 112 can be a square wave or a sine wave, and in general is a lower (voltage) level, continuous power signal, in various embodiments.

Transformer 114 receives the signal generated by generator 112 and amplifies the signal at a second, high voltage side of transformer 114. The high side of transformer 114 is coupled with output filter circuitry 130.

Second transformer stage 120 comprises an AC generator 122 and a transformer 124. Generator 122 provides a power signal to a first, low voltage side of transformer 124. In some embodiments, generator 122 is distinct from generator 112, while in other embodiments generators 122 and 112 are one and the same. In contrast with the lower level, continuous power signal generated by generator 112, however, generator 122 generates a signal that comprises a series of repetitive high power, short duration bursts. Transformer 124 receives the signal generated by generator 122 and amplifies the signal at a second, high voltage side of transformer 124. The high side of transformer 124 is coupled with output filter circuitry 130.

Output filter circuitry 130 comprises a capacitor 132 and an inductor 134 arranged in series, and a capacitor 136 and an inductor 138 arranged in parallel with one another. Thus, capacitor 132 and inductor 134 form a series resonant LC output filter, and capacitor 136 and inductor 138 form a parallel resonant LC output filter.

Those skilled in the art will recognize that other configurations and variations of circuitry 100 (as well as other circuitry depicted and discussed herein) are possible in other embodiments. For example, transformer 114 can comprise a center-tapped transformer as depicted or two push-pull transformers in parallel, among other possibilities. Additionally, other configurations of filter circuitry 130 also are possible in various embodiments.

Figure 2:
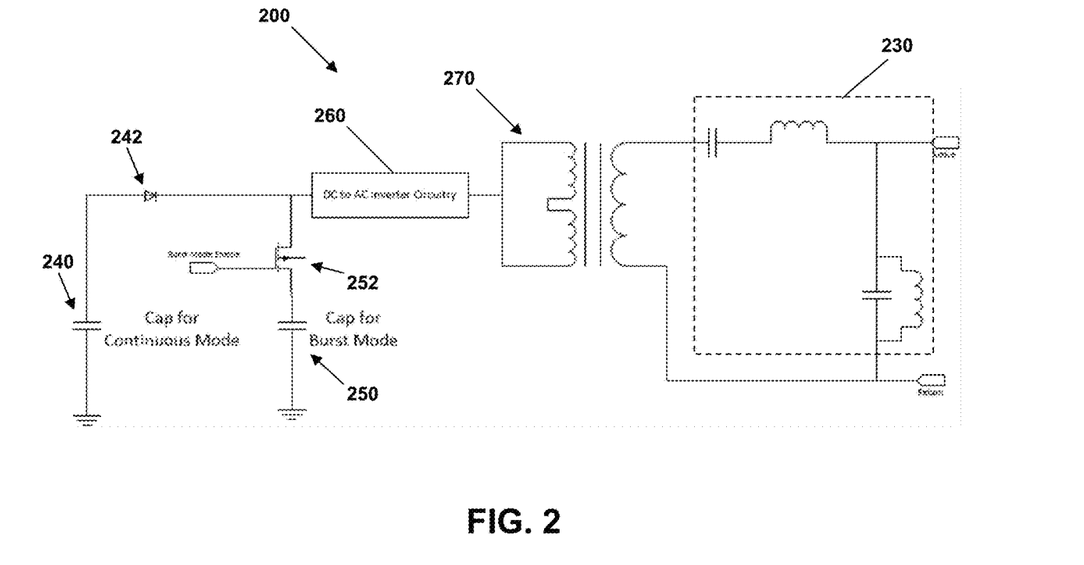
FIG. 2 depicts a transformer circuit diagram according to another embodiment.

Another embodiment of electrosurgery generator circuitry 200 is depicted in FIG. 2. In contrast with the circuitry 100 of FIG. 1, circuitry 200 comprises capacitors arranged to drive the voltage in both the first (continuous) and second (burst) stages or modes.

In particular, circuitry 200 comprises a first capacitor 240, a diode 242, a second capacitor 250, a field effect transistor (FET) 252, direct current (DC) to AC inverter circuitry 260, a transformer 270 and output filter circuitry 230. Output filter circuitry 230 is similar to or the same as output filter circuitry 130 and will not be discussed again here in light of the discussion above with respect to FIG. 1.

First capacitor 240 is associated with the lower (voltage) level, continuous power signal discussed with respect to transformer 114 in FIG. 1. In operation, charge stored by first capacitor 240 is used to drive the continuous mode voltage. Diode 242 is arranged to prevent voltage from second capacitor 242 from "backing up" and charging first capacitor 240. In other words, diode 242 functions like a one-way valve in circuitry 200.

Second capacitor 250 is associated with the burst signal discussed above with respect to transformer 124 in FIG. 1. In operation, charge stored by second capacitor 250 is used to drive the burst mode voltage and provide a signal that comprises a series of repetitive high power, short duration bursts. FET 152 is arranged on the high side of capacitor 250 and functions as a switch to turn on or off the signal from second capacitor 250.

Signals from both first capacitor 240 and second capacitor 250 are provided to DC to AC inverter circuitry 260, with the resultant signal provided from inverter circuitry 260 to the low side of transformer 270. The output signal from the high side of transformer 270 is provided to filter circuitry 230, which can be the same as or similar to filter circuitry 130 discussed above with respect to FIG. 1.

Figure 3:
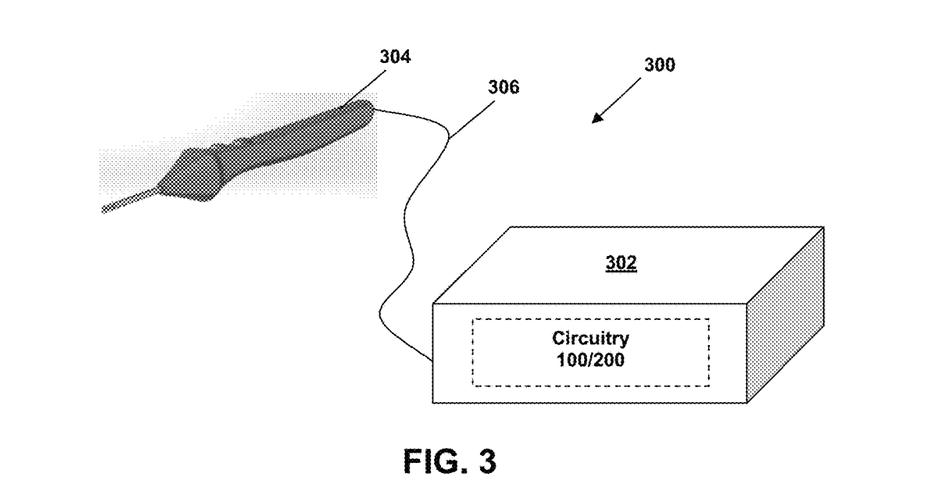
FIG. 3 depicts an electrosurgical system according to an embodiment.

FIG. 3 is a diagram of an embodiment of an electrosurgical system 300 that can comprise circuitry 100 or circuitry 200. System 300 comprises an electrosurgical generator unit 302 mechanically and electrically coupled with an electrosurgical probe device 304 by a cable 306. Electrosurgical generator unit 302 comprises circuitry 100 or 200, along with one or more processors and other circuitry and components known to electrosurgical generators, and is operable to generate signals that are communicated via cable 306 to electrosurgical probe device 304, which itself is operable to treat patient tissue (e.g., by cutting or coagulating) in electrosurgical procedures.

Electrosurgical probe device 304 is one example of an electrosurgical device that can be used with embodiments discussed herein. Particular examples include INTACT and PLASMABLADE devices available from MEDTRONIC, INC. Various embodiments can comprise other electrosurgical devices or tools, as essentially any electrosurgical or electrocautery tool can be compatible with embodiments discussed herein.

In operation, circuitry 100 or 200, as part of electrosurgical generator unit 302, is configured to generate a signal having an amplitude modulated waveform with varying power levels to provide consistent and clean electrosurgical cutting by electrosurgical probe device 304 at an overall reduced power level. In one embodiment, this is accomplished by generating a first signal that comprises a low level of continuous power and modulating or combining this signal with a plurality of repetitive high power, short duration bursts. One example of such an amplitude modulated signal is depicted in FIG. 4, which shows a continuous, lower level power portion 480 and a plurality of higher power, shorter duration bursts 490.

Figure 4:
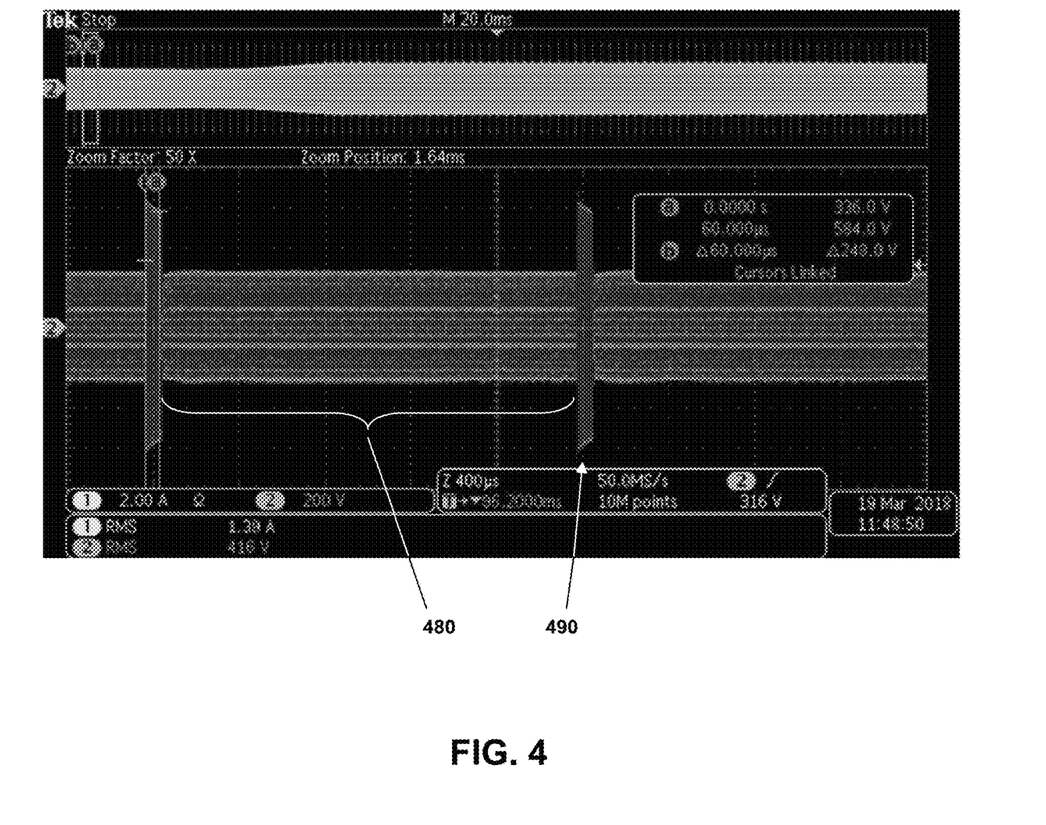
FIG. 4 depicts a signal waveform on an oscilloscope screen according to an embodiment.

In one example, each burst 490 is about 10 microseconds (μs) to about 100 μs long, such as about 60 μs in the example of FIG. 4, with about 2 milliseconds (ms) to about 10 ms off-time between sequential bursts 490. FIG. 4 shows about 2 ms of off-time between the two bursts 490 depicted. While the voltage of continuous portion 480 is lower, generally less than about 400 volts (V), such as about 330 V peak (about 230 V RMS) in the example of FIG. 4, the voltage during each burst 490 can be higher than about 400 V, such as more than 500 V peak, or about 600 V peak (about 420 V RMS) in FIG. 4. Put another way, superimposing bursts 490 on continuous portion 480 can provide a combined signal that requires a lower average RMS power for the signal while providing similar or improved electrosurgical effects on the tissue.

Figure 5:
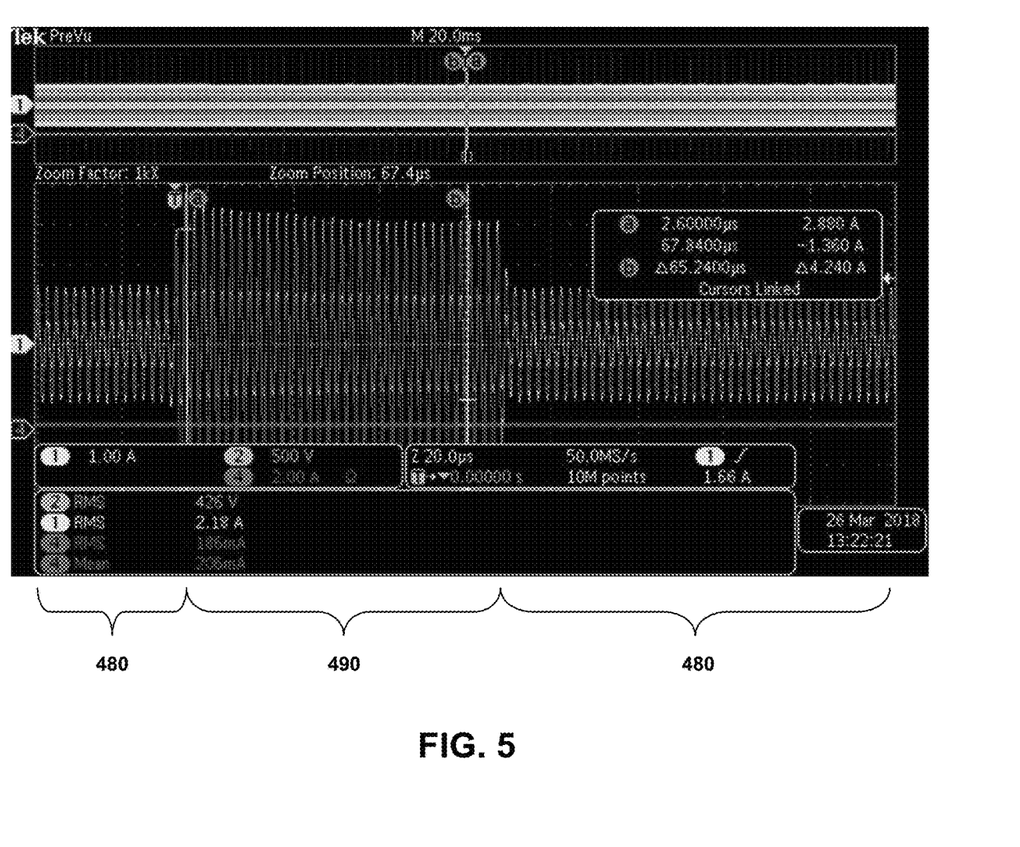
FIG. 5 depicts a signal waveform on an oscilloscope screen according to an embodiment.
Figure 6:
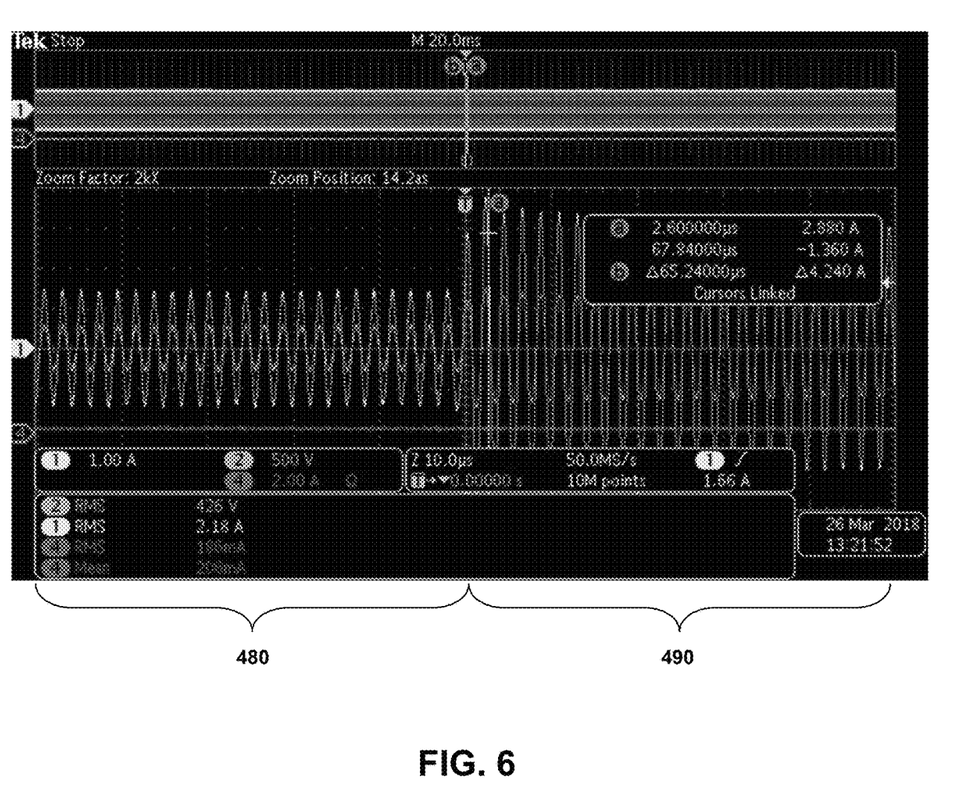
FIG. 6 depicts a signal waveform on an oscilloscope screen according to an embodiment.

The superimposition or combination of the higher-amplitude burst waveform (490) on or with the lower-amplitude continuous waveform (480) can be seen in FIGS. 5 and 6. Both waveforms (480) and (490) are sinusoidal. The sinusoidal signal has a frequency between about 400 kiloHertz (kHz) and 500 kHz in some embodiments, such as about 470 kHz in the example of FIGS. 4-6. Each burst 490 may be damped, which can be seen most easily in FIG. 5.

The example frequencies, voltages, timings and other signal parameters included herein can vary in other embodiments. In some cases, these and other signal parameters can be adjusted, scaled or selected by a user via electrosurgical generator unit 302. In one embodiment, electrosurgical generator unit 302 provides pre-programmed modes from which a user can select an operating mode. In other embodiments, electrosurgical generator unit 302 can enable a user to adjust pre-programmed modes or settings or create custom modes or settings. Modes can be programmed or created, or parameters for modes can be adjusted, for particular procedures, types of tissue (e.g., skin, muscle, fat), or according to other factors. In some embodiments, electrosurgical generator unit 302 can comprise sensors or some other feedback mechanism via which a mode can be selected or parameter adjusted based on real-time characteristics sensed or received during a procedure. This can enable the burst portions of the signal to be turned on or off, algorithmically, only as needed based on real-time surgical conditions. In another embodiment, plasma detection can be detected by measuring tissue load impedance during use of system 300, and providing the burst mode signals when measured tissue load impedance is low (i.e., below a predetermined threshold).

An advantage of embodiments of circuitry 100, 200 discussed herein is that the higher power, shorter duration bursts (490) can incite or restart plasma while the lower power, continuous signal (480) provides enough power to maintain plasma. Thus, superimposing the higher-amplitude burst waveform (490), with the bursts repeated with sufficient frequency, on the lower-amplitude continuous waveform (480) can sustain desired tissue cutting even at power levels low enough to allow occasional collapse of plasma. This can provide clean and efficient tissue cutting, with lower drag and significantly reduced thermal impact on the tissue cut (e.g., as shown via histology testing) compared to a continuous high power setting conventionally required to prevent plasma breakdown. In other words, less power can be needed, and fewer thermal effects created, for the same drag force of the probe. In some embodiments, this can reduce thermal artifact and allow for plasma blade-like cutting even with probes that do not have a dielectric (e.g., glass) coating. Another way to consider the bursts (490) and continuous signal (480) is that the bursts (490) are a coagulation mode superimposed on (or combined with) a continuous sinusoid cutting mode.

Features and components of different embodiments discussed herein can be combined in other embodiments. In this way particular signal effects can be designed and achieved in order to meet particular desires or needs in the industry.

Various embodiments of systems, devices, and methods have been described herein. These embodiments are given only by way of example and are not intended to limit the scope of the claimed inventions. It should be appreciated, moreover, that the various features of the embodiments that have been described may be combined in various ways to produce numerous additional embodiments. Moreover, while various materials, dimensions, shapes, configurations and locations, etc. have been described for use with disclosed embodiments, others besides those disclosed may be utilized without exceeding the scope of the claimed inventions.

Persons of ordinary skill in the relevant arts will recognize that the subject matter hereof may comprise fewer features than illustrated in any individual embodiment described above. The embodiments described herein are not meant to be an exhaustive presentation of the ways in which the various features of the subject matter hereof may be combined. Accordingly, the embodiments are not mutually exclusive combinations of features; rather, the various embodiments can comprise a combination of different individual features selected from different individual embodiments, as understood by persons of ordinary skill in the art. Moreover, elements described with respect to one embodiment can be implemented in other embodiments even when not described in such embodiments unless otherwise noted.

Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims, it is expressly intended that the provisions of 35 U.S.C. § 112(f) are not to be invoked unless the specific terms "means for" or "step for" are recited in a claim.

The invention claimed is:

1. An electrosurgical system comprising:
an electrosurgical signal generator operable to generate an amplitude modulated power signal that combines a first continuous sinusoidal signal having a first peak voltage configured to generally maintain previously generated plasma with a plurality of discrete second sinusoidal burst signals configured to incite generation of plasma, the amplitude modulated power signal having a second peak voltage greater than the first peak voltage when the plurality of discrete second sinusoidal burst signals are combined with the first sinusoidal signal portion;
an electrosurgical probe electrically coupled with the electrosurgical signal generator to receive the amplitude modulated power signal and apply the amplitude modulated power signal as an output such that the amplitude modulated power signal generates plasma at a cutting end of the electrosurgical probe with the burst signals and generally maintains the plasma at the cutting end between burst signals; and wherein the system further comprises:
a first capacitor configured to store a first voltage for the first sinusoidal signal portion;
a second capacitor configured to store a second voltage for the plurality of second sinusoidal signal portions;
DC to AC inverter circuitry;
a field effect transistor coupling the second capacitor to the DC to AC inverter circuitry;
a transformer coupled with the first capacitor and the second capacitor via the DC to AC inverter circuitry; and
filter circuitry electrically coupled between the transformer and the electrosurgical probe.

2. The electrosurgical system of claim 1, further comprising a cable electrically coupling the electrosurgical probe to the electrosurgical signal generator.

3. The electrosurgical system of claim 1, wherein the electrosurgical signal generator further comprises:
a first transformer configured to provide the first sinusoidal signal portion;
a second transformer configured to provide the plurality of second sinusoidal signal portions; and
filter circuitry electrically coupled between both the first transformer and the second transformer and the electrosurgical probe.

* * * * *